United States Patent [19]
Fujita et al.

[11] 4,021,198
[45] May 3, 1977

[54] METHOD FOR DETECTING CYSTINE AND CYSTEINE

[75] Inventors: Tadashi Fujita, Sakai; Takehisa Chiba, Amagasaki; Masato Horiuchi, Toyonaka, all of Japan

[73] Assignee: Santen Pharmaceutical Co. Ltd., Osaka, Japan

[22] Filed: Mar. 31, 1976

[21] Appl. No.: 672,348

Related U.S. Application Data

[63] Continuation-in-part of Ser. No. 507,467, Sept. 19, 1974, abandoned.

[30] Foreign Application Priority Data

Oct. 8, 1973  Japan .............................. 48-113070

[52] U.S. Cl. ................................................ 23/230 B
[51] Int. Cl.$^2$ ........................................ G01N 33/16

[58] Field of Search ................................. 23/230 B

[56] References Cited
OTHER PUBLICATIONS

Rosenthal et al., Anal. Abstr. 19,5093 (1970).
Hawk et al., Practical Physiol. Chemistry, McGraw–Hill, 1954, p. 141.
Mosby Co., pub., Gradwohl's Clinical Laboratory Methods and Diagnosis, 7th Edn., edited by Frankel et al., p. 1923.

*Primary Examiner*—Robert M. Reese
*Attorney, Agent, or Firm*—Flynn & Frishauf

[57] ABSTRACT

Method for detecting cystine or cysteine which comprises adding a reducing agent and a metallic compound which liberates nickel ion or cobaltous ion and observing a color change.

16 Claims, No Drawings

METHOD FOR DETECTING CYSTINE AND CYSTEINE

RELATED APPLICATION

This application is a continuation-in-part of application Ser. No. 507,467, filed Sept. 19, 1974 and now abandoned.

This invention relates to a coloring composition for the detection of cystine or cysteine in a solution and a method of detection therefor. It is known that both cystine and cysteine are sulfur-containing amino acids and are easily convertible to each other by oxidation and/or reduction.

There have been various methods to detect cystine or cysteine. They include polarographic, cyanide-nitroprusside, iodine-nitride, Sullivan and Fleming Vassel methods. However, these known methods require a long time for detection. These methods also require reagents which should be prepared at the time of use, and which are poisonous, thus causing careful and troublesome handling. It is generally known that organic thiol compounds reveal color by forming complexes with various kinds of heavy metallic ions, but methods for detecting cysteine or cystine by making use of this reaction are not practical because the color reaction is not sensitive.

We have conducted further research and finally found a coloring composition for detecting cystine or cysteine and a detecting method therefor. The principle is as follows.

Cysteine itself or cysteine which is produced by the reduction of cystine forms complexes with heavy metallic ions in the presence of certain kinds of heavy metallic ions and reducing agents.

In addition to this reaction, sulfide ion ($S^{2-}$) is released from the reducing agent itself or by the reaction between the reducing agent and cysteine.

The sulfide ion binds to the complex and forms a mixed ligands complex. We have found that by the formation of the mixed ligands complex, the presentation of color becomes remarkable and the coloration occurs in a short time.

On the basis of these findings, we have developed a very sensitive coloring composition to detect cystine or cysteine easily and quickly: said coloring composition comprises a reducing agent which reduces cystine to cysteine and releases sulfide ion by itself or by the reaction with cysteine, and a metallic compound which liberates nickel ion or cobaltous ion. We have also developed a method for detecting cystine or cysteine in solution by using said coloring composition.

Metallic compounds of nickel ion or cobaltous ion used in the present invention are organic acid salts such as acetates, and inorganic acid salts such as sulfates, nitrates, chlorides and hydroxides.

Reducing agents used in the present invention include alkali dithionites and alkali borohydrides. They reduce cystine to cysteine and also release $S^{2-}$ by the reaction with cysteine.

It is also possible to use an alkali sulfide or an alkali hydrosulfide as a reducing agent. An alkali sulfide or alkali hydrosulfide forms a mixed ligands complex with $S^{2-}$ ions which have already been present; however, at the same time, it reacts with cobaltous ion or nickel ion to form a metallic sulfide which sometimes makes color indistinct. In such case, however, it is possible to make it clear with the separation of the metallic sulfide.

Brown color is developed when a solution containing cystine or cysteine is added to the coloring composition of the present invention.

It is easy to check the absence of cystine or cysteine in solution if the color of the solution is different from brown. For this purpose, it is desirable to add a chelating agent to the coloring composition, which forms a water-soluble chelate compound by reaction with nickel ion or cobaltous ion to give such a color as blue, green or red when a solution contains no cystine or cysteine. Suggested chelating agents include ethylenediaminetetraacetates (EDTA), nitrilotriacetate, tartrate and citrates.

It is desirable to maintain the solution at pH 6.0–8.5 because the color reaction proceeds at pH 6.0–8.5 easily. It is therefore desirable to add a buffer agent such as tris (hydroxymethyl) aminomethane phosphate, dipotassium hydrogen-phosphate-sodium dihydrogen phosphate, boric acid-sodium borate or a combination thereof.

The coloring composition of this invention can be used in the form of a solution of each compound, but it can also be offered in the form of powders, granules, pellets and tablets because it is more convenient and practical to use. The coloring composition can be used without using fillers, but it is recommended to add such water-soluble fillers as soluble starch, glucose, sorbitol, sucrose, mannitol, etc., because it is quite convenient for use and efficient for weighing out the coloring composition.

It is also possible to change the degree or limit of coloration by changing the amount of the component in the coloring composition. It is possible to determine cystine or cysteine content by absorptiometry. But it is also possible to estimate cysteine or cystine content by eye-observation.

By virtue of this speedy check ability, there are many fields of application of this composition. Medical diagnosis, for example, for cystinuria which shows abnormally increased cystine in urine, is one interesting field of application. Namely, with the coloring composition, the procedure required is only to add urine to the composition. If it contains an abnormal degree of cystine (cystinuric urine), it turns brown within a few minutes at room temperature, and that is one important feature of the present invention. Hence, this invention offers a novel coloring composition and novel method for not only the diagnosis of a cystinuria, but also the detection in an earlier stage of latent cystinuria by group medical examinations.

The present invention is further illustrated by the following examples, but they are not to be construed as limiting the present invention.

EXAMPLE 1

1. 9.0 ml. of 5% borate buffer (pH 7.2) containing 100 μg/ml. cystine was prepared. Into this buffer 1.0 ml. of 3.44 mM metallic compound (3.44 μmol) listed hereunder and 15 mg. sodium dithionite (86 μmol) were added. Thus, the mol ratio is 1/25 (metallic compound/dithionite). After standing for 5 minutes, the color of this sample solution was observed with the eye and its absorbance was also determined at 400 mμ against a control solution. The control solution had been prepared in the same manner as the sample solution except for the use of 5% borate buffer containing no cystine. As shown hereunder, cobaltous and nickel compounds are useful to detect cystine among metallic compounds.

solution. After 5 minutes, the absorbance and color of each sample solution were observed against a control

| Metallic Compound | | | Absorbance | Color with the Eye | |
|---|---|---|---|---|---|
| | | | | Sample Solution | Control Solution |
| Cobaltous | acetate | (4 $H_2O$) | 1.360 | brown | light pink |
| | sulfate | (7 $H_2O$) | 1.365 | '' | '' |
| | nitrate | (6 $H_2O$) | 1.364 | '' | '' |
| | hydroxide | | 0.323 | '' | '' |
| | chloride | (6 $H_2O$) | 1.310 | '' | '' |
| Nickel | nitrate | (6 $H_2O$) | 0.358 | '' | light green |
| | sulfate | (6 $H_2O$) | 0.286 | '' | '' |
| | hydroxide | (1 $H_2O$) | 0.307 | '' | '' |
| | carbonate | (4 $H_2O$) | 0.154 | '' | '' |
| Cupric | sulfate | (5 $H_2O$) | 0.062 | light blue | light blue |
| | chloride | (2 $H_2O$) | 0.060 | '' | '' |
| | nitrate | (3 $H_2O$) | 0.060 | '' | '' |
| | acetate | (1 $H_2O$) | 0.059 | '' | '' |
| Ferric | sulfate | (6 $H_2O$) | 0.015 | light yellowish brown | light yellowish brown |
| Ferrous | sulfate | (7 $H_2O$) | 0.010 | '' | '' |
| Ferric | chloride | (3 $H_2O$) | 0.017 | '' | '' |
| Ammonium ferrous sulfate | | (6 $H_2O$) | 0.036 | '' | '' |
| Ammonium ferric sulfate | | (24 $H_2O$) | 0.015 | '' | '' |

2. The experiments of (1) were modified in such a way as to change the concentration of metallic compound in order to study the effect on the coloration. Nickel nitrate was used as the metallic compound. As shown hereunder, the degree of coloration increases with the nickel ion concentration.

| Concentration of nickel nitrate (mM) | Molar Ratio Nitrate/Dithionite | Absorbance After 1 minute |
|---|---|---|
| 1.13 | 1/76 | 1.503 |
| 0.85 | 1/101 | 0.455 |
| 0.71 | 1/121 | 0.252 |
| 0.57 | 1/150 | 0.043 |
| 0.43 | 1/200 | 0.003 |
| 0.28 | 1/307 | 0.000 |

3. 10 ml. of 5% borate buffer (pH 7.2) containing 100 μg/ml. cystine and 2.0 ml. of 100 μg/ml. nickel nitrate (0.7 μmol) were mixed. Various kinds of reducing agents listed hereunder were added to the resulting solution. As shown hereunder, all the reducing agents gave visible brown color to the sample solution, although some deeply and others lightly.

| Reducing Agent | Nitrate/Dithionite Molar Ratio | Absorbance | Color with the Eye | |
|---|---|---|---|---|
| | | | Sample Solution | Control Solution |
| Sodium dithionite (15 mg) (86 μmol) | 1/123 | 0.337 | brown | light green |
| Potassium borohydride (5 mg) (93 μmol) | 1/133 | 0.552 | '' | colorless |
| Sodium sulfide (9$H_2O$) (5 mg) (21 μmol) | 1/30 | 0.955* | '' | '' |
| Sodium hydrosulfide (5 mg) (89 μmol) | 1/127 | 0.894* | '' | '' |

*Absorbance of the supernatant after centrifugation.

4. The experiments of (3) were modified in such a way as to change the amount of the reducing agent in order to study the effect on the coloration. Sodium dithionite was used as the reducing agent. The results hereunder show that the degree of coloration increases with the amount of sodium dithionite.

| Weight of Reducing Agent (mg) | Nitrate/Dithionite Molar Ratio | Absorbance | | Color with Eye |
|---|---|---|---|---|
| | | After 1 minute | After 5 minutes | After 5 minutes |
| 7.5 (43 μmol) | 1/61 | 0.140 | 0.143 | brown |
| 15.0 (86 μmol) | 1/123 | 0.328 | 0.324 | deep brown |
| 30.0 (172 μmol) | 1/244 | 0.470 | 0.525 | '' |
| 45.0 (258 μmol) | 1/366 | 0.504 | 0.537 | '' |

5. The effect of chelating agent on the color was studied. One ml. of several kinds of 0.35 M chelating agent (350 μmol), 1 ml. of 0.4 M metallic compound (400 μmol) and 10 mg. of sodium dithionite (57 μmol) were added to 10 ml. of 5% borate buffer containing 100 μg.ml. cystine. The chelating agent/metallic compound/dithionite molar ratio was 0.88/1/0.14. After standing for 3 minutes, the color of this sample solution was observed against a control solution. The control solution was prepared in the same manner as the sample solution except for the use of 5% borate buffer which contains no cystine.

As shown hereunder, all the sample solutions show brown color, while the control solutions show various colors more deeply than the case of no addition of chelating agent. It has become apparent that a chelating agent facilitates distinguishing between the same solution and control solution.

| Metallic Compound: | Nickel Nitrate | | Cobaltous Sulfate | |
|---|---|---|---|---|
| Chelating Agent | Sample Solution | Control Solution | Sample Solution | Control Solution |
| no addition | brown | light green | brown | light pink |
| disodium edetate (EDTA) | brown | blue | brown | pink |
| nitrilotriacetate | brown | green | brown | pink |
| sodium citrate | brown | green | brown | pink |
| sodium tartrate | brown | green | brown | pink. |

6. Relationship between the degree of coloration and pH was studied. One ml. of 40 mM of nickel sulfate (40 μmol) and 5 mg. of sodium dithionite (29 μmol), in a molar ratio of 1/0.73, were added to 9 ml. of several kinds of buffer (0.1 M) containing 100 μg/ml. cystine. As shown hereunder, it is desirable to keep the solution at pH 6.0–8.5.

| Buffers | pH | Absorbance |
|---|---|---|
| 0.1 M borate | 5.0 | 0.037 |
| " | 6.0 | 0.185 |
| " | 6.5 | 0.352 |
| " | 7.2 | 0.481 |
| " | 7.5 | 0.736 |
| " | 8.5 | 0.148 |
| " | 9.2 | 0.037 |
| 0.1 M phosphate | 7.5 | 0.118 |
| 0.1 M tris(hydroxymethyl) aminomethane-sodium dihydrogen phosphate | 7.5 | 0.243 |

EXAMPLE 2

The color of the solution, which was prepared by mixing soluions or chemicals listed hereunder, was observed in a series of experiments (1) – (4).

| Chemicals | Concentration or Weight | Remarks |
|---|---|---|
| Heavy Metallic compound: | | |
| Nickel nitrate | 40 mM | |
| Nickel sulfate | 40 mM | |
| Cobaltous nitrate | 40 mM | |
| Cobaltous sulfate | 40 mM | |
| Chelating agent: EDTA | 10 mM | |
| Reducing agent: | | |
| Sodium dithionite | 5 mg.* | powder |
| Buffer: Borate | 5 % | pH 7.2 |
| Cystine solution | 100 μg/ml. | Buffer was used as the solvent |
| Cysteine solution | 100 μg/ml. | " |

*(29 μmol; nitrate/dithionite molar ratio, 1/0.73).

1. Effect of sodium ditionite on the cysteine coloration

| No. | Nickel Nitrate Solution | Nickel Sulfate Solution | Cysteine Solution | Sodium Dithionite | Color After 5 Minutes |
|---|---|---|---|---|---|
| 1 | 1 ml.** | — | 10 ml. | — | light reddish brown |
| 2 | 1 ml.** | — | 10 ml. | 5 mg.*** | deep brown |
| 3 | — | 1 ml.** | 10 ml. | — | light reddish brown |
| 4 | — | 1 ml.** | 10 ml. | 5 mg.*** | deep brown. |

**(40 μmol; nitrate or sulfate/dithionite molar ratio, 1/0.73)
***(29 μmol).

The light reddish brown solutions of Nos. 1 and 3 take their color from the colored complex formed by nickel ion with cysteine. This coloration is not sensitive to cysteine because it is faint. As can be seen in the case of solutions Nos. 2 and 4, addition of sodium dithionite results in deep brown color solutions.

2. Effect of sodium dithionite on the cystine coloration

| No. | Nickel Nitrate Solution | Nickel Sulfate Solution | Cystine Solution | Sodium Dithionite | Color After 5 Minutes |
|---|---|---|---|---|---|
| 5 | 1 ml.** | — | 10 ml. | 5 mg.*** | deep brown |
| 6 | 1 ml.** | — | 10 ml. | — | water white |
| 7 | — | 1 ml.** | 10 ml. | 5 mg.*** | deep brown |
| 8 | — | 1 ml.** | 10 ml. | — | water white. |

( and * as above).

Solutions Nos. 5 and 7 show the same deep brown color as the solutions Nos. 2 and 4, but Nos. 6 and 8 do not show any color because a reducing agent is absent.

3. Coloration in the present or absence of cystine

| No. | Nickel Nitrate Solution | Nickel Sulfate Solution | Cystine Solution | Buffer | Sodium Dithionite | EDTA[a] | Color After 5 minutes |
|---|---|---|---|---|---|---|---|
| 9 | 1 ml** | — | — | 10 ml | 5 mg*** | — | light green |
| 10 | 1 ml** | — | — | 10 ml | 5 mg*** | 1 ml | blue |
| 11 | 1 ml** | — | 10 ml | — | 5 mg*** | 1 ml | deep brown |
| 12 | — | 1 ml** | — | 11 ml | 5 mg*** | — | light green |
| 13 | — | 1 ml** | — | 10 ml | 5 mg*** | 1 ml | blue |
| 14 | — | 1 ml** | 10 ml | — | 5 mg*** | 1 ml | deep brown |

( and * as above)
(a = 10 μmol)
(molar ratio nitrate or sulfate/dithionite/EDTA = 1/0.73/0.25).

Solutions Nos. 9 and 12 do not show brown color because they contain no cystine, but show light green color of nickel ion. Solutions Nos. 10 and 13, which were prepared by adding EDTA to solutions Nos. 9 and 12, show blue color which is due to a colored complex of nickel ion with EDTA. Solutions Nos. 11 and 14 which contain cystine show deep brown color.

4. Coloration by using cobaltous ion instead of nickel ion

| No. | Cobaltous Sulfate Solution | Cobaltous Nitrate Solution | Buffer | Cystine Solution | Sodium Dithionite | EDTA | Color After 5 minutes |
|---|---|---|---|---|---|---|---|
| 15 | 1 ml. | — | 10 ml. | — | 5 mg. | 1 ml. | light pink |
| 16 | 1 ml. | — | — | 10 ml. | 5 mg. | 1 ml. | brown |
| 17 | — | 1 ml. | 10 ml. | — | 5 mg. | 1 ml. | pink |
| 18 | — | 1 ml. | — | 10 ml. | 5 mg. | 1 ml. | brown |

(concentrations and molar ratios as in (3) above).

In the case where cobaltous ion (4) was used instead of nickel ion (3), results were similar as to coloration reaction.

EXAMPLE 3

1. 1.0 ml. of 41 mM nickel nitrate (41 μmol), 15 mg. sodium dithionite (86 μmol) and 1.0 ml. of 3 mM EDTA (3 μmol) were added to 2 ml. of 5% borate buffer containing cystine in various concentrations. The molar ratio nitrate/dithionite/EDTA was 1/2.1/0.07. After standing for 5 minutes their absorbances were measured. As described hereunder, a calibration line which followed Beer's law was obtained from the results. The results showed that cystine can be assayed by this method.

| Cystine Concentration (μg/ml) | Absorbance |
|---|---|
| 0 | 0.009 |
| 50 | 0.198 |
| 100 | 0.407 |
| 150 | 0.611 |
| 200 | 0.805. |

2. In the same manner as (1) except for the use of cobaltous sulfate instead of nickel nitrate, the relationship between cystine concentration and absorbance was examined. In this case, a calibration line was also obtained.

| Cystine Concentration (μg/ml) | Absorbance at 400 mμ |
|---|---|
| 0 | 0.000 |
| 50 | 0.102 |
| 100 | 0.260 |
| 150 | 0.442 |

-continued

| Cystine Concentration (μg/ml) | Absorbance at 400 mμ |
|---|---|
| 200 | 0.608. |

EXAMPLE 4

5. 60 mg.γ-globulin, which was dissolved in 1.0 ml. of water and 4.0 ml. of 1 N HCl, was hydrolyzed by heating in a boiling water bath. After one hour, the solution was then neutralized by adding 1 N NaOH and diluted to 8.0 ml. with water. To 1.0 ml. (contains 7.5 mg. γ-globulin) of this solution were added reagents which were employed in Example 3, above. The absorbance at 400 mμ showed 0.587 (140μg) after 5 minutes. This value, when calculated by the calibration line in Example 3, corresponded to 20.0 μg. cystine per 1 mg. γ-globulin. This roughly equaled 20.8 μg. cystine/mg. γ-globulin which is the known amount in the literature. Cystine content of bovine serum albumin was also measured in a similar manner and the resulting value, 22.0 μg/mg., also roughly equaled the known amount 22.6 μg/mg in the literature.

EXAMPLE 5

Reagents A, B, C and D listed hereunder were prepared.

| Reagent | Nickel Nitrate | Cobaltous Sulfate | Sodium Dithionite[x] | EDTA[y] | Nitrate or Sulfate/ Dithionite/ EDTA, Molar Ratio | Buffer* |
|---|---|---|---|---|---|---|
| A | 11.0 (37.8 μmol) | — | 2.2 | 8.8 | 1/0.89/0.62 | 38.0 |
| B | 15.0 (51.6 μmol) | — | 2.2 | 8.8 | 1/0.45/0.46 | 34.0 |
| C | 20.0 (68.8 μmol) | — | 2.2 | 8.8 | 1/0.28/0.34 | 29.0 |
| D | — | 20.0 (71.1 μmol) | 2.2 | 8.8 | 1/0.18/0.33 | 29.0 | x = 12.6 μmol; y = 23.6 μmol; (unit = mg.)
*Powder consisting of 5.2 g. sodium hydrogen carbonate, and 0.4 g. sodium dihydrogen phosphate.

2 ml. of urine containing cystine in various concentrations was added to the reagent. After standing for 1 minute, the color of the urine was observed with the eye. Four panelists were engaged in the examination and each panelist took the reagent and examined five times about one urine sample at random. The results of the examinations were presented by the marks according to the following method. If a panelist decides the urine to be positive, one mark is given to the judgment, 0.5 mark to Pseudo positive and 0 mark to negative. The results were as follows:

| Cystine Content (μg/ml.) | Reagent A | Reagent B | Reagent C | Reagent D |
|---|---|---|---|---|
| 5 | 0 | 0 | 16 | 0 |
| 10 | 0 | 4.5 | 20 | 0 |
| 20 | 0 | 10.5 | 20 | 0 |
| 30 | 4.5 | 18 | 20 | 0 |
| 40 | 9.5 | 20 | 20 | 3 |
| 50 | 16 | 20 | 20 | 9.5 |
| 60 | 20 | 20 | 20 | 16 |
| 85 | 20 | 20 | 20 | 20 |
| 100 | 20 | 20 | 20 | 20 |
| 200 | 20 | 20 | 20 | 20 |

Note:
If all panelists judge one urine sample as positive in 5 examinations, the sample gains 20 marks, i.e. 1 mark × 5 times × 4 panelists = 20.

As is obvious from the results listed above, urine containing more than 60 μg/ml., 40 μg/ml. and 10 μg/ml. cystine would be detected with an accuracy of 100% by using the reagents A, B and C, respectively. Urine containing more than 50 μg/ml., 30 μg/ml. and 5 μg/ml. cystine could be detected with accuracy of 80 – 90% also by using the reagents A, B and C, respectively. By using reagent D, which contained 20 mg. of cobaltous sulfate instead of nickel nitrate, urine containing 60 μg/ml. cystine can be detected with an accuracy of 80% and 85 μg/ml. cystine with an accuracy of 100%.

EXAMPLE 6

Pellets were prepared which consist of 16.5 mg. nickel sulfate, 4.0 mg. sodium dithionite, 50.0 mg. sodium hydrogen carbonate, 4 mg. sodium dihydrogen phosphate and sucrose. The sulfate/dithionite molar ratio was 1/0.37. A pellet is 400 mg. in weight by addition of an adequate amount of sucrose.

Urine samples containing 30 μg/ml., 50 μg/ml., 100 μg/ml., 150 μg/ml. and 200 μg/ml. cystine were also prepared by dissolving cystine in normal urine (cystine content = 10 μg/ml.). By the use of the pellets, ten panelists (A–J) examined twice the urine samples in a similar manner as in Example 5 except for the addition of 4 ml. of the sample urine. As shown in the following Table, all the panelists showed negative for normal urine, pseudo positive for the urine containing 30 μg/ml. of cystine, and positive for the urine containing more than 50 μg/ml. cystine. The cyanide-nitroprusside method, that is famous for detecting cystine, was compared with the method of the present invention. These results showed that the method of the present invention is superior to the cyanide-nitroprusside method in practical use because the latter method always requires fresh solutions of sodium cyanide and sodium nitroprusside, and it requires more than 10 minutes for the detection of cystine. On the other hand, the method offered by the present invention requires only 2 or 3 minutes for the detection of cystine and can be used in safety whenever one wishes to make an examination with a pellet.

Sensitivity test of pelletized reagent for detection of cystine

| | Cystine content (μg/ml) | 10 | | 30 | | 50 | | 100 | | 150 | | 200 | |
|---|---|---|---|---|---|---|---|---|---|---|---|---|---|
| Panelist | Times of test | 1st | 2nd | 1st | 2nd | 1st | 2nd | 1st | 2nd | 1st | 2nd | 1st | 2nd |
| A | | − | − | ± | ± | + | + | + | + | + | + | + | + |
| B | | − | − | ± | ± | + | + | + | + | + | + | + | + |
| C | | − | − | ± | ± | + | + | + | + | + | + | + | + |
| D | | − | − | ± | ± | + | + | + | + | + | + | + | + |
| E | | − | − | ± | ± | + | + | + | + | + | + | + | + |
| F | | − | − | ± | ± | + | + | + | + | + | + | + | + |
| G | | − | − | ± | ± | + | + | + | + | + | + | + | + |
| H | | − | − | ± | ± | + | + | + | + | + | + | + | + |
| I | | − | − | ± | ± | + | + | + | + | + | + | + | + |
| J | | − | − | ± | ± | + | + | + | + | + | + | + | + |

Judgement −: negative, ±: pseudo positive, +: positive

The molar ratio of reducing agent to the metallic compound (containing Ni and/or Co) can vary widely as shown by experimental results given above. The ratios shown are from about 0.15 to about 370. Preferably, the ratio ranges from about 0.7 to about 250.

When a chelating agent is used together with the reducing agent and metallic compound, the reducing agent/metallic compound molar ratio can also be varied widely, e.g., from about 0.15 to about 3 and preferably from about 0.15 to about 2. The molar ratio of reducing agent to chelating agent is not critical; preferably, it is from about 0.15 to about 30.

Complexes of a reducing agent, a metallic compound and cystine or cysteine contain varying quantities of each component. Generally, the molar relationships are from about 7 to about 65 moles of reducing agent, from about 0.15 to about 100 moles of metallic compound, per mole of cystine or cysteine.

What we claim is:

1. A method for detecting cystine or cysteine in solution, which comprises contacting a solution containing cystine or cysteine with a reagent comprising
    i. a reducing agent which reduces cystine to cysteine and releases sulfide ion ($S^{2-}$) by itself or by reaction with cysteine; and
    ii. a metallic compound which liberates nickel ion or cobaltous ion, each of cystine and cysteine forming a mixed ligands complex with the nickel ion or cobaltous ion and sulfide ion ($S^{2-}$) with the formation of a brown color.

2. The method of claim 1, wherein the reagent contains a buffer agent to maintain the pH of the reagent from 6.0 to 8.5.

3. The method of claim 1, wherein the molar ratio of the reducing agent to the metallic compound is from about 0.15 to about 370.

4. The method of claim 1, wherein the reducing agent is selected from the group consisting of an alkali metal dithionite, an alkali metal borohydride, an alkali metal sulfide and an alkali metal hydrosulfide.

5. The method of claim 1, wherein the metallic compound is selected from the group consisting of an acetate, sulfate, nitrate, chloride and hydroxide.

6. The method of claim 1, wherein the reagent contains a chelate which forms a soluble chelate with the nickel ion or cobaltous ion.

7. The method of claim 6, wherein the reagent contains a buffer agent to maintain the pH of the reagent from 6.0 to 8.5.

8. The method of claim 6, wherein the molar ratio of the reducing agent to the metallic compound is from about 0.15 to about 3.

9. A diagnostic method for detecting the presence or absence of cystinuria, which comprises adding urine to a reagent comprising
   i. a reducing agent which reduces cystine to cysteine and releases sulfide ion ($S^{2-}$) by itself or by reaction with cysteine, and
   ii. a metallic compound which liberates nickel ion or cobaltous ion, each of cystine and cysteine forming a mixed ligands complex with the nickel ion or cobaltous ion and sulfide ion ($S^{2-}$), with the formation of a brown color.

10. The method of claim 9, wherein the reagent contains a buffer agent to maintain the pH of the reagent from 6.0 to 8.5.

11. The method of claim 9, wherein the reducing agent is selected from the group consisting of an alkali metal dithionite, an alkali metal borohydride, and alkali metal sulfide and an alkali metal hydrosulfide.

12. The method of claim 9, wherein the metallic compound is selected from the group consisting of an acetate, sulfate, nitrate, chloride and hydroxide.

13. The method of claim 9, wherein the molar ratio of the reducing agent to the metallic compound is from about 0.15 to about 370.

14. The method of claim 13, wherein the molar ratio of the reducing agent to the metallic compound is from about 0.15 to about 250.

15. The method of claim 9, wherein the reagent contains a chelate which forms a soluble chelate with the nickel ion or cobaltous ion.

16. The method of claim 15, wherein the reagent contains a buffer agent to maintain the pH of the reagent from 6.0 to 8.5.

* * * * *

UNITED STATES PATENT AND TRADEMARK OFFICE
CERTIFICATE OF CORRECTION

PATENT NO. : 4,021,198
DATED : May 3, 1977
INVENTOR(S) : TADASHI FUJITA et al

It is certified that error appears in the above-identified patent and that said Letters Patent are hereby corrected as shown below:

Column 8, line 20: replace "5. 60" with --- 60 ---.

Signed and Sealed this

Eleventh Day of October 1977

[SEAL]

Attest:

RUTH C. MASON
Attesting Officer

LUTRELLE F. PARKER
Acting Commissioner of Patents and Trademarks